(12) United States Patent
Liu

(10) Patent No.: US 12,274,891 B2
(45) Date of Patent: Apr. 15, 2025

(54) STABLE SMART LASER HAIR-GROWING INSTRUMENT WITH INDEPENDENT LIGHT SOURCES

(71) Applicant: Shenzhen Lescolton Electrical Appliance Co., Ltd., Shenzhen (CN)

(72) Inventor: Jianwen Liu, Guangdong (CN)

(73) Assignee: Shenzhen Lescolton Electrical Appliance Co., Ltd., Shenzhen (CN)

( * ) Notice: Subject to any disclaimer, the term of this patent is extended or adjusted under 35 U.S.C. 154(b) by 429 days.

(21) Appl. No.: 17/824,328

(22) Filed: May 25, 2022

(65) Prior Publication Data
US 2023/0338743 A1  Oct. 26, 2023

(30) Foreign Application Priority Data
Apr. 24, 2022  (CN) .......................... 202210434912.4

(51) Int. Cl.
*A61N 5/06* (2006.01)
*A61N 5/067* (2006.01)
*H05K 1/02* (2006.01)

(52) U.S. Cl.
CPC .......... *A61N 5/0617* (2013.01); *A61N 5/067* (2021.08); *A61N 2005/0632* (2013.01); *A61N 2005/0647* (2013.01); *A61N 2005/0651* (2013.01)

(58) Field of Classification Search
CPC .................. A61N 5/0617; A61N 5/067; A61N 2005/0632; A61N 2005/0647; A61N 2005/0651; A61N 2005/0652; A61N 2005/0626; A61N 1/0456; A61N 1/36021; A61N 1/36071; A61N 1/36017; A61N 1/36153; A61N 1/36171; A61N 1/36135; A61N 1/36132; H05B 45/30; H05K 1/02; H05K 1/144; H05K 2201/10106; A61B 2562/166; A61B 3/0008; A61B 5/0077; A61B 5/6898

See application file for complete search history.

(56) References Cited

U.S. PATENT DOCUMENTS

| | | | |
|---|---|---|---|
| 8,591,561 B2 | 11/2013 | Kinoshita et al. | |
| 9,132,279 B2 | 9/2015 | Roersma et al. | |
| 9,795,443 B2 | 10/2017 | Van Hal et al. | |
| 9,833,633 B2 | 12/2017 | Hamid et al. | |
| 10,518,106 B2 | 12/2019 | Roersma et al. | |
| 2021/0315353 A1* | 10/2021 | Kim | A45D 20/122 |
| 2021/0315357 A1* | 10/2021 | Kim | F21V 3/00 |

* cited by examiner

*Primary Examiner* — Carl H Layno
*Assistant Examiner* — Anh-Khoa N Dinh
(74) *Attorney, Agent, or Firm* — JEEN IP LAW, LLC

(57) ABSTRACT

A stable smart laser hair-growing instrument with independent light sources includes a shell, a laser emitting assembly and a control system; the shell is provided with a cavity disposed above a user's head, the laser emitting assembly includes light sources, a first circuit board and multiple second circuit boards, the first circuit board is disposed in the shell at a position aligned at a center of a user head; a gap is arranged between the adjacent second circuit boards; the light sources are evenly distributed on the first circuit board and those of the second circuit boards; the control system includes a circuit control and a multi-group of independent control units electrically connected with the circuit control; all the independent control units are electrically connected to the corresponding driving circuit of the second circuit boards and that of the first circuit board, respectively.

8 Claims, 9 Drawing Sheets

STABLE SMART LASER HAIR-GROWING INSTRUMENT WITH INDEPENDENT LIGHT SOURCES

FIELD OF THE INVENTION

The present invention relates to beauty device technology field, particularly, relates to a stable smart laser hair-growing instrument with independent, light sources.

BACKGROUND OF THE INVENTION

A core technology of a laser hair growing instrument is LLLT (low intensity laser therapy), a red light with 655 nm wavelength is used to activate vitality of hair follicles, accelerate blood circulation in a scalp and nutrition absorption of the hair follicle, reduce DHT (dihydro) on the hair follicles, promote ATP (adenosine triphosphate) as cellular energy to normally release and promote hair growth. It also can regulate oil secretion, relieve the scalp tension, such as with drugs and nutrient solution can help nutrients and drugs better absorption.

Multiple medical organizations, such as University of Miami Miller School of Medicine, Department of Dermatology in University of Minnesota, Department of Dermatology, Clevel and Clinic, has developed clinical research about LLLT on hair growth. Patients with alopecia between 25 and 60 years old underwent with 26 weeks of LLLT, the results demonstrated that the total response rate reached 93% for men and 90% for women.

Most traditional hair growing instrument have the following structures: including a helmet and light sources. The helmet is worn on a human head, laser-ray output directions of the light sources are aligned to a scalp of the human head. After start up, the light sources output low-energy lasers to a preset position of the human head, thereby achieving the stimulating hair growth effect. However, in order to adapt the shape of the human head, most of the traditional hair growing instruments use the flexible circuit board as the circuit carriers. Correspondingly, the structure of the flexible circuit board is integrated. Once some part of the circuit in the circuit board fails, the whole flexible circuit board will be paralyzed, thus affecting the use of the whole hair growing instrument. Therefore, the traditional hair growing instrument is short service life, low practicability and low stability.

SUMMARY OF THE INVENTION

The object of the present invention is to provide a stable smart laser hair-growing instrument with independent light sources, aiming to resolve the shortcomings that the hair-growing instrument in the prior art adopts a flexible circuit board as a circuit carrier. Once some part of the flexible circuit board damages, the entire flexible circuit board is paralyzed, thereby the whole hair-growing instrument can not be used.

In order to achieve the above object, the present invention provides a stable smart laser hair-growing instrument with independent light sources, which includes a shell, a laser emitting assembly and a control system; the shell is provided with a cavity disposed above a user's head, the laser emitting assembly includes light sources, a first circuit board and multiple second circuit boards, the first circuit board is disposed in the shell at a position aligned at a center of a user head; the multiple second circuit boards are multiple rings with concentric axes, arranged up and down, in the adjacent two ring, an outer diameter of the one at below is bigger than that of the one at above. A gap is arranged between the adjacent two rings. The light sources are evenly distributed on an end surface, facing the user's head, of the first circuit board and of the second circuit boards. The first circuit board and each of the second circuit boards are provided with a driving circuit, respectively. The light sources are electrically connected with the corresponding driving circuit. The control system includes a circuit control and a multi-group of independent control units electrically connected with the circuit control. All the independent control units are electrically connected to the corresponding driving circuit of the second circuit boards and that of the first circuit board, respectively.

Each of the light sources includes a light-emitting LED and a laser light unit, which are integrated on the second circuit boards or the first circuit board, and electrically connected with the driving circuit on the correspondingly circuit boards.

Each of the light, sources also includes a loading unit for assembling the light-emitting LED and the laser light unit. The loading unit is fixed on the second circuit, boards or the first circuit board. The loading unit is a seal sleeve structure filled with xenon.

The multiple of loading units are welded on the second circuit boards and the first circuit board. The multiple of the loading units assembled with the light-emitting LED and the laser light units are arranged at intervals along the rings of the second circuit boards, each of the second circuit boards and the corresponding light sources on it forms an annular lamp strip structure.

The shell includes a base and a frame. The cavity is formed in the base, the frame is disassembly connected with an end of the base away from the cavity. The first circuit board and the second circuit boards are arranged between the base and the frame. The base is provided with multiple of through holes, each aligned to one of the corresponding light sources, the lights of the light sources can pass through the through holes and enter the cavity.

The through holes are designed as long holes, evenly distributed on the base. A portion of the through holes, respectively aligned with the corresponding second circuit boards, are arranged in an arc-shaped structure. The other portion of the through holes, aligned with the first circuit board, are arranged in a linear structure.

The base is provided with a human body sensing mechanism facing to the user's head, contained in the cavity. The output end of the human body sensing mechanism is electrically connected with the circuit control.

The inner wall of the base is provided with a clamp mechanism which includes two lateral forehead assemblies and a frontal forehead assembly. The two lateral forehead assemblies are symmetrically positioned along an opening edge of the cavity and aligned with the left and right forehead of the user, respectively. The frontal forehead assembly is disposed at the opening edge of the cavity and aligned to the frontal forehead of the user. A holding slot capable of holding the user's head is formed between the lateral forehead assemblies and the frontal forehead assembly. The human body sensing mechanism is provided on the lateral forehead assemblies.

The lateral forehead assemblies includes a mounting frame and a cushion. The mounting frame is disassembly mounted on an inner wall of the base. Then an end of the mounting frame is provided with a bending part, the bending part extends towards the cavity, the cushion is fixed on the bending part. The bending part and the mounting frame are made of elastic material, and the cushion is made of sponge or silicone.

The human sensing mechanism includes a sensing circuit and a sensing unit. The sensing circuit is disposed in the shell. The sensing unit is fixed on the lateral forehead assembly. The sensing circuit is electrically connected with the circuit control. The sensing unit is either a pressure sensor or an infrared sensor.

One or more of the above technical schemes in the stable smart laser hair-growing instrument with independent light sources provided by the embodiment of the invention have at least one of the following technical effects:

The second circuit boards are distributed up and down surrounding the first circuit board. The first circuit board and the second circuit boards are disposed independently, and each of the second circuit boards is provided independently. The circuit units on the first circuit board and on each of the second circuit boards are disposed independently, and electrically connected with the circuit control through the multi-group of independent control units, respectively. When the first circuit board or any of the second circuit boards is faulty or short circuited, the remaining circuit boards operate normally. In, the actual using process, unless the power supply is faulty, the light sources, electrically connecting with the first circuit board and the second circuit boards, work independently, without interference. And the light sources are distributed in the rings arranged up and down, thereby fully covering any part of the user's head. Most of the hair growing instrument in the prior art adopt a flexible circuit board as the circuit carrier. Once some part of the circuit board fails, the entire flexible circuit board is paralyzed, thereby the whole hair growing instrument can not be used. In the embodiment, the light sources are distributed in the rings arranged up and down, the light sources, located in different circuit parts are disposed independently from each other through the independent control units, when one of the circuit boards is faulty, the other circuit boards can operate normally, thereby promising the light sources to operate stably, which can improve the hair growing effect.

BRIEF DESCRIPTION OF THE DRAWINGS

In order to explain more clearly the technical scheme in the embodiments of the invention, a brief introduction is given below to the attached drawings needed in the embodiments or the prior art description. Obviously, the attached drawings in the following description are only some embodiments of the invention. For ordinary technicians in this field, other drawings can be obtained according to these drawings without paying creative labor.

DETAILED DESCRIPTION OF ILLUSTRATED EMBODIMENTS

Figure 1:
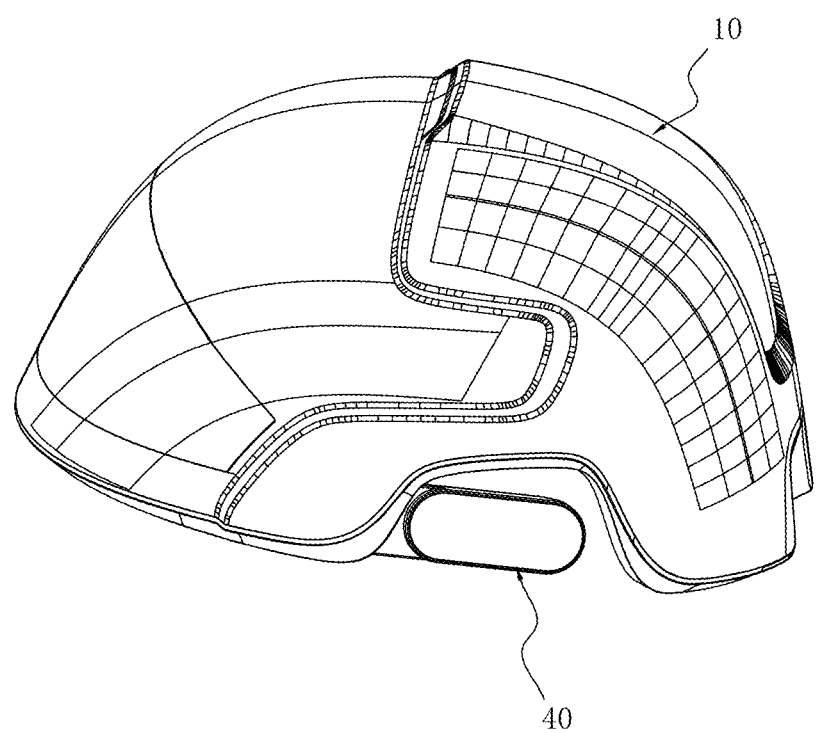
FIG. 1 is a perspective view of the stable smart laser hair-growing instrument with independent light sources according to the invention.

The embodiments of the present invention are described in details below, and the embodiments are shown in the attached figures, where the same or similar label from beginning to end represents the same or similar element or element with the same or similar function. The embodiments described below by reference to FIGS. 1-6 are exemplary and are intended to be used to explain embodiments of the present invention and can not be understood as limitations to the present invention.

In the description of the embodiment of the present invention, it needs to be understood that the azimuth or position relation indicated in the terms "length", "width", "upper", "lower", "front", "rear", "left", "right", "vertical", "horizontal", "top", "bottom", "inside", "outside" and so on are based on the azimuth or position relation shown in the attached drawing, only for the convenience of describing the embodiment of the present invention and simplifying the description, rather than indicating or implying that the device or element must have a specific orientation, with a specific orientation and operation, so it can not be understood as a limitation to the present invention.

Furthermore, the Willis "first", "second" are used only for descriptive purposes and it can not be understood as indicating or implying relative importance or implicitly the number of technical features indicated. Thus, the qualification of "first" and "second" features may include one or more of them explicitly or implicitly. In the description of the embodiments of the invention, the meaning of "multiple" is two or more, unless otherwise specified.

In the embodiment of the invention, unless other specified and qualified, the terms "installation", "connection", "fixed" and other terms shall be broadly understood, for example, it may be fixed connection, detachable connection, or integration; it may be mechanical connection or electrical connection; it may be directly connected or indirectly connected by intermediate media, it may be internal connection of two components or the interaction of two components. For ordinary technicians in the field, the specific meaning of the above term in the embodiment of the invention can be understood according to the specific circumstances.

In an embodiment according to the present invention, it provides a stable smart laser hair-growing instrument with independent light sources, which includes a shell 10, a laser emitting assembly 20 and a control system 50. The shell 10 is provided with a cavity 13 disposed above the user's head.

The laser emitting assembly 20 includes light sources 21, a first circuit board 22 and multiple second circuit boards 23. The first circuit board 22 is disposed in the shell 10 at a position aligned at a center of a user head. The multiple second circuit boards 23 are multiple rings with concentric axes, arranged up and down, in the adjacent two ring, an outer diameter of the one at below is bigger than that of the one at above. A gap 26 is arranged between the adjacent two rings. The light sources 21 are evenly distributed on end surface, facing the user's head, of the first circuit board 22 and those of the second circuit boards 23. The first circuit board 22 and each of the second circuit boards 23 are provided with a driving circuit 27, respectively. The light sources 21 are electrically connected with the corresponding driving circuit 27. The control system 50 includes a circuit control 51 and a multi-group of independent control units 52 electrically connected with the circuit control 51. All the independent control units 52 are electrically connected to the corresponding driving circuit 27 of the second circuit boards 23 and that of the first circuit board 22, respectively.

Figure 5:
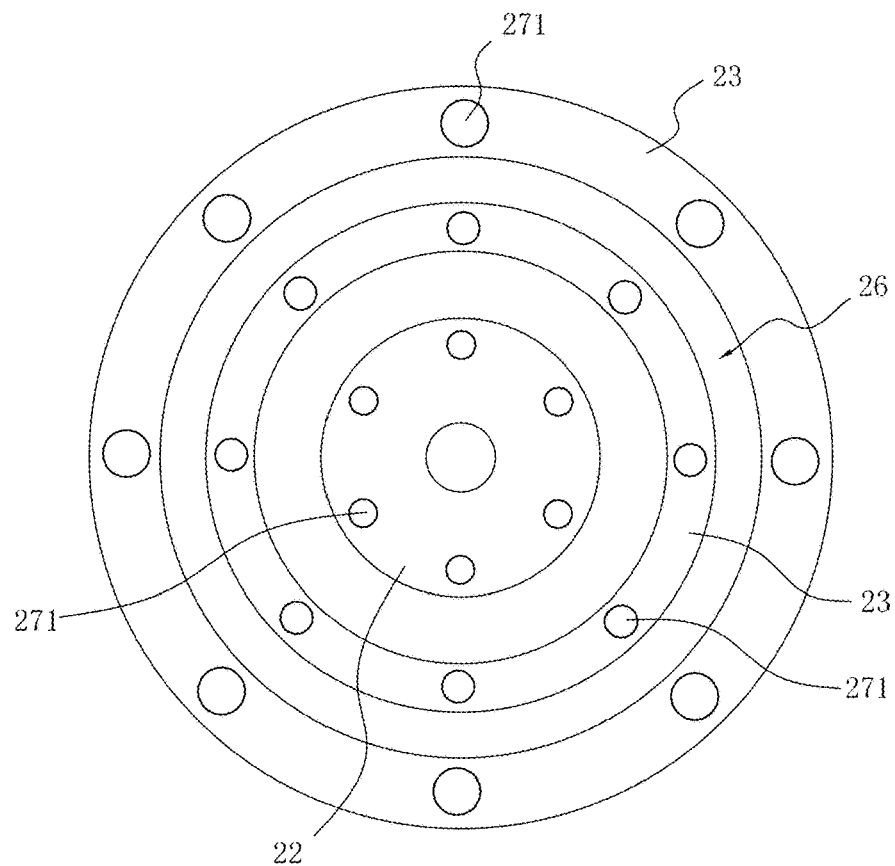
FIG. 5 is a top view of the laser emitting assembly according to the invention.

Referring to FIG. 5, in the embodiment, the driving circuit 27 includes a multi-group of circuit units 271, which are assembled along the rings of the second circuit board 23. The circuit units 271 are provided with multiple of power supply control terminals. Each of the light sources 21 are correspondingly arranged on one of the power supply control terminals. The first circuit board 22 is designed as a disk-like structure. All the second circuit boards 23 are intervals arranged up and down around the first circuit board 22 according to the length of their outer diameter.

Figure 4:
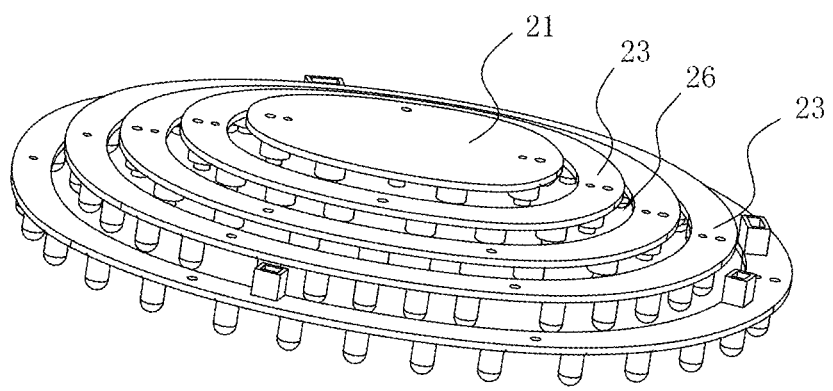
FIG. 4 is a perspective view of the laser emitting assembly according to the invention.

Specifically, referring to FIG. 4 and FIG. 5, the second circuit boards 23 are distributed up and down surrounding the first circuit board 22. The first circuit board 22 and each of the second circuit boards 23 are disposed independently. The circuit units 271 on the first circuit board 22 and on each of the second circuit boards 23 are also disposed independently, and electrically connected with the circuit control 51 through the multi-group, of independent control units 52, respectively. When the first circuit board 22 or any of the second circuit boards 23 is damaged or short circuited, the remaining circuit boards operate normally. In the actual using process, unless the power supply is damaged, the light sources 21, electrically connecting with the first circuit board 22 and the second circuit boards 23, work independently, without interference. And the light sources 21 are distributed in the rings arranged up and down, thereby fully covering any part of the user's head.

Most of the hair growing instrument in the prior art adopt a flexible circuit board as the circuit carrier. Once some part of the circuit board is damaged, the entire flexible circuit board is paralyzed, thereby the whole hair growing instrument can not be used. In the embodiment, the light sources 21 are distributed in the rings arranged up and down, the light sources 21 located in different circuit parts are disposed independently from each other through the independent control units 52, when one of the circuit boards is damaged, the other circuit boards can operate normally, thereby ensuring the light sources 21 to operate stably, which can improve the hair growing effect.

Figure 6:
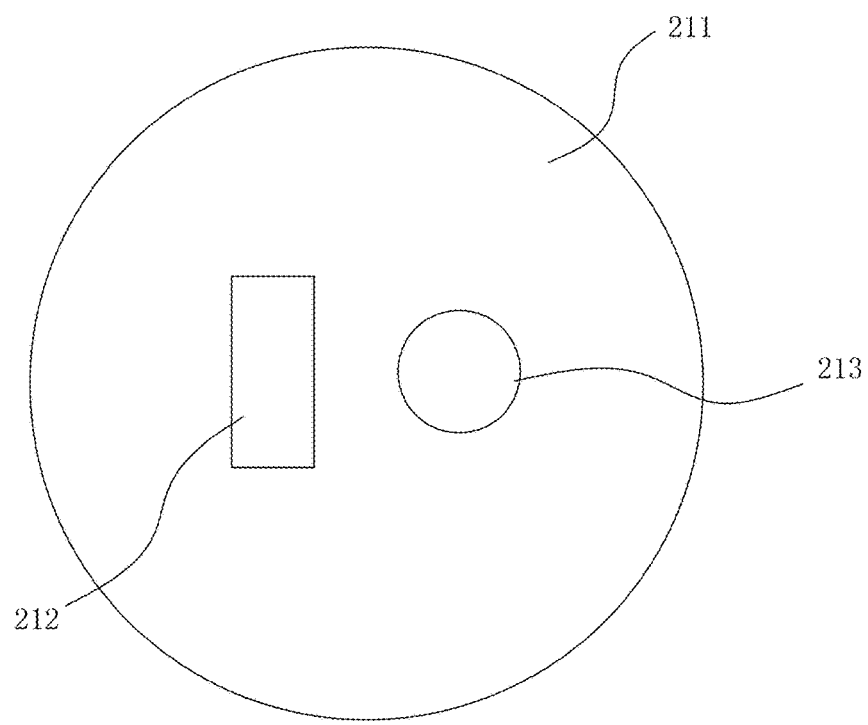
FIG. 6 is a bottom view of the light sources 21 according to the invention.

Referring to FIG. 6, in the other embodiment, each of the light sources 21 includes a light-emitting LED 212 and a laser light unit 213. The light-emitting LED 212 and the laser light unit 213 are integrated on the second circuit board 23 or the first circuit board 22. Both of the light-emitting LED 212 and the laser light unit 213 are electrically connected with the correspondingly driving circuit 27 on the correspondingly circuit boards. Adopting two types of lighting methods, it is beneficial to improve the ray intensity of the light sources 21 and improve the hair growing effect.

Referring to FIG. 6, in another embodiment, each of the light sources 21 also includes a loading unit 211 for assembling the light-emitting LED 212 and the laser light unit 213. The loading unit 211 is fixed on the second circuit boards 23 or the first circuit board 22. The loading unit 211 is a seal sleeve structure filled with xenon. Because the xenon has an extremely high luminous intensity, the xenon lamp is beneficial to improve the light emitting effect of the light sources 21 and improve the hair growing efficiency.

Referring to FIG. 4-6, in another embodiment, the loading units 211 are welded on the second circuit boards 23. Multiple of the loading units 211 assembled with the light-emitting LEDs 212 and the laser light units 213 are arranged at intervals along the rings of the second circuit boards 23, each of the second circuit boards 23 and the corresponding light sources 21 on it, foul's an, annular lamp strip structure. Adopt welding, methods instead of the traditional pasted LED, it is beneficial to improve the structure stability of the light sources 21 and prevent the light sources 21 from being heated and disassembled in the process of light emission, thereby prolong the service life of the hair-growing instrument.

Referring to FIG. 1, FIG. 2, FIG. 7 and FIG. 8, in another embodiment, the shell 10 includes a base 11 and a frame 12. The cavity 13 is formed in the base 11 the frame 12 is disassembly connected with an end of the base 11 away from the cavity 13. The first circuit board 22 and the second circuit boards 23 are arranged between the base 11 and the frame 12. The base 11 is provided with multiple of through holes 24, each aligned to one of the corresponding light sources 21, the lights of the light sources 21 can pass through the through, holes 24 and enter the cavity 13.

Figure 2:
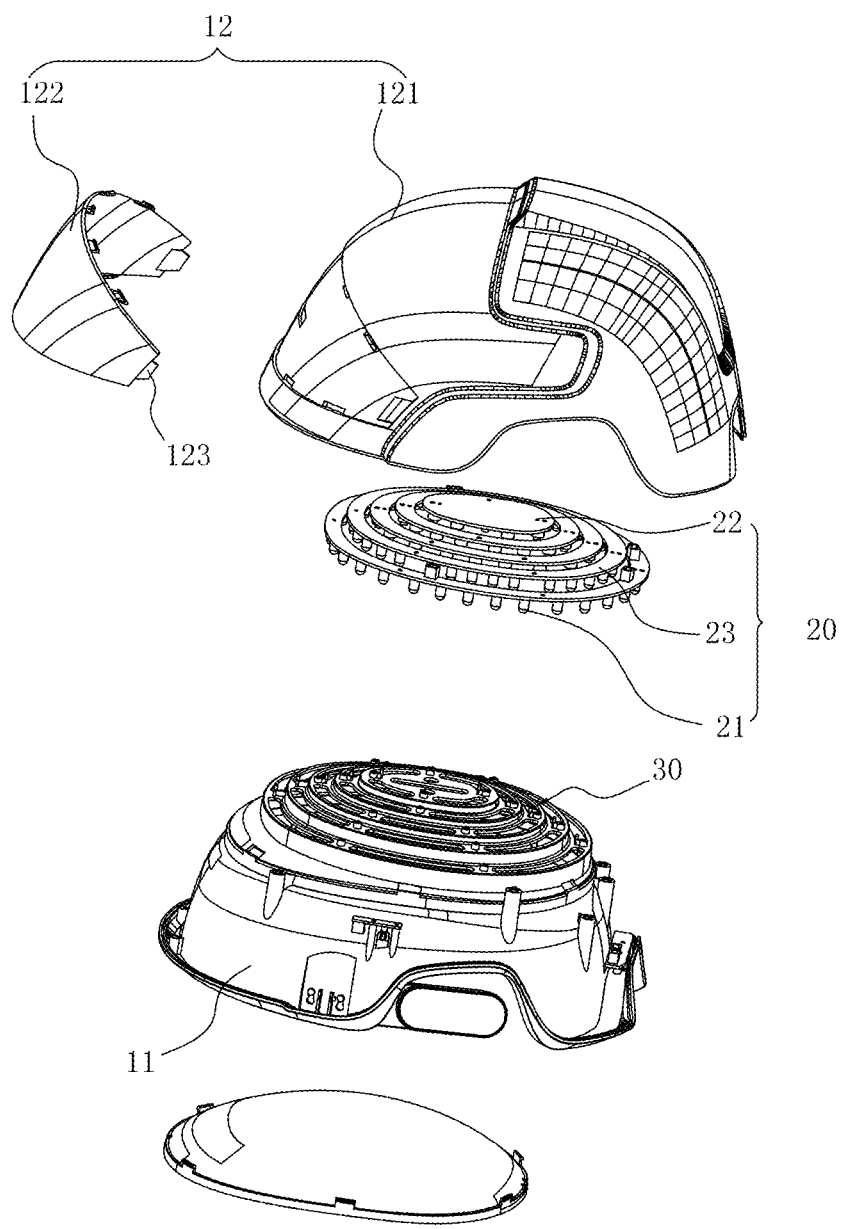
FIG. 2 is an exploded view of the stable smart laser hair-growing instrument with independent light sources showing in FIG. 1.
Figure 9:
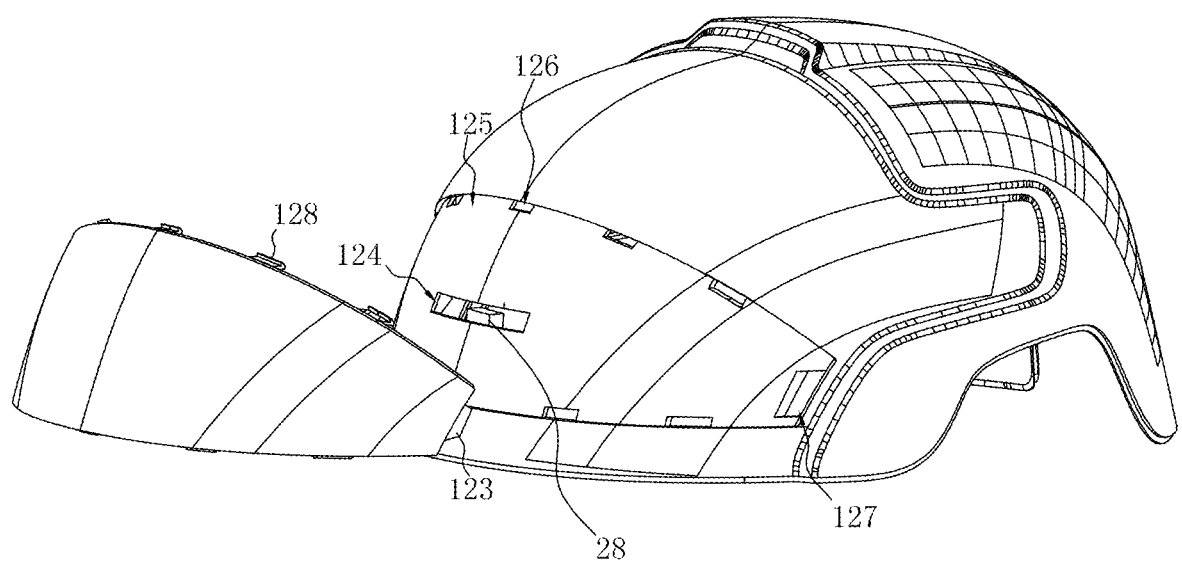
FIG. 9 is a perspective view of the frame according to the invention.

Referring to FIG. 2 and FIG. 9, in the embodiment, the frame 12 includes a frame body 121 and a refractive plate 122. The frame body 121 covers the base 11. The refractive plate 122 is disassembly mounted on the frame body 121. The frame body 121 is provided with a mounting hole 121 facing the refractive plate 122. The light sources 121 includes an indicating light 28 arranged in the mounting hole 124. The indicating light 28 is electrically connected with the circuit control 51. The light of the indicating light 28 spreads outside through the refractive plate 122 to indicate the operating state of the hair growing instrument.

Specifically, referring to FIG. 9, an end of the frame body 121 closing to the refractive plate 122 is provided with a mounting slot 125 used for clamping the refractive plate 122. The mounting hole 124 is formed in the mounting slot 125. The refractive plate 122 is in an arc shape, similar to one integral goggles in the prior art. The refractive plate 122 is made of PVC, acrylic or glass material. A penetration slot 126 is provided at the edge position of the mounting slot 125. The edge of the refractive plate 122 is provided with an inverted structure 128 connected to the slot 126. Both ends of the refractive plate 122 are respectively provided with a positioning insert 123. The edge position, corresponding to both, ends of the refractive plate 122, of the mounting slot 125 is provided with a limiting slot 127. The limiting slot 127 is clamped with the positioning insert 123. The positioning insert 123 is in a plate shape, and the end of the positioning insert 123, away from the refractive plate 123, gradually narrowed, so that the end of the positioning insert 123 can smoothly enter the limiting slot 127.

The mounting hole 124 is a rectangular hole, the size of the mounting hole 124 is much less than that of the refractive plate 122. A cross section of the refractive plate 122 is in an arc shape and a middle position of the refractive plate 122 is raised back to the frame body 121. The refractive plate 122 is designed as a concave lens structure with respect to the indicating light 28 in the mounting hole 124. The light emitted by the indicating light 28 is refracted by the refractive plate 122 to realize the diffusion effect, thereby improving the indicating effect.

Figure 10:
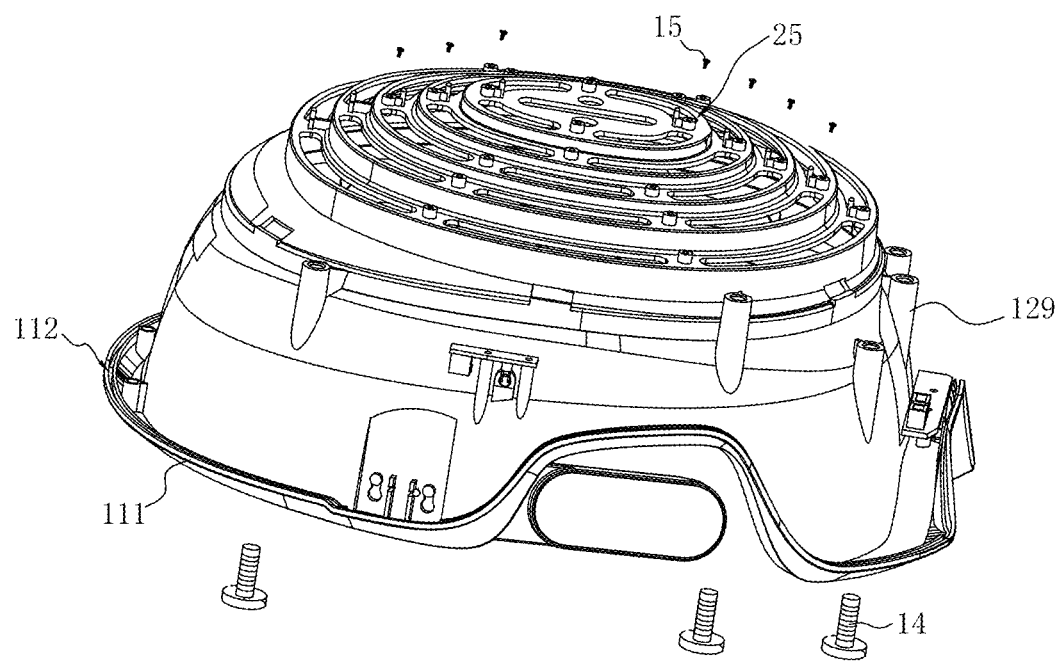
FIG. 10 is a perspective view of the studs and the pre-tighten screws taking off the base according to the invention.

In the embodiment, referring to FIG. 10, both of the base 11 and the frame 12 are disposed as a hemispherical helmet-like structure. The frame is locked at the end of the base 11 away from the cavity 13 by locating studs 129 and screws 14. Specifically, the base 11 is provide with a ring-shaped side rib 111 at a side wall closed to the opening. An end of the ring-shaped side rib 111 close to the frame 12 is formed with a few positioning slots 112 for clamping with an edge of the frame 12.

Figure 8:
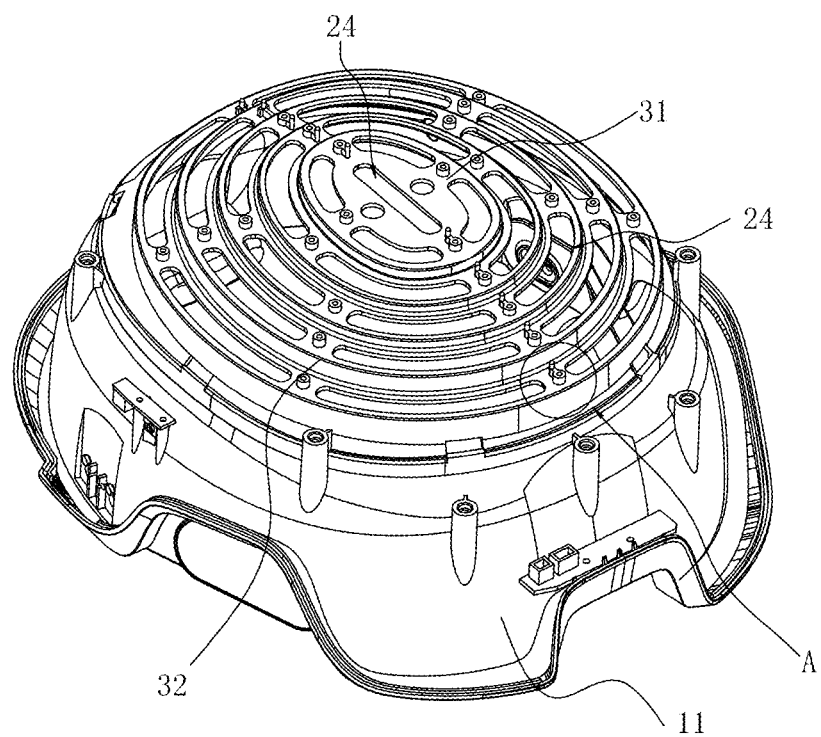
FIG. 8 is a perspective view of the mounting step according to the invention.

Referring to FIG. 2 and FIG. 8, in the embodiment, the end of the base 11, away from the cavity 30, is provided with a mounting step 30 for installing the second circuit boards 23 and the first circuit board 22. The mounting step 30 includes a first mounting step 31 and second mounting steps 32. The first mounting step 31 is located at a end of the base 11 aligned to a user's head top. The first mounting step 31 is provided with multiple of studs 25 and locked with the first circuit board 22 by the cooperation of the studs 25 and pre-tighten screws 15. The number of the second mounting steps 32 is multiple groups and the second mounting steps 32 are arranged in a ring-shaped structure.

Referring to FIG. 5, in the embodiment, the second mounting steps 32 in a top view angle is designed as a ring-shaped structure. The second mounting steps 32 surround the first mounting step 31. The outer diameters of the second mounting steps 32 are gradually increased in an outward direction from the first mounting station step 31. All of the second mounting steps 32 are concentric and individually used for mounting the second circuit boards 23 with a corresponding outer diameter. The through holes 24 are formed in the second mounting steps 32. The second mounting steps 32 are provided with the studs 25 at locations between the through holes 24. The second circuit boards 23 are locked on the second mounting steps 32 by the screws 14.

In the embodiment, the heights of all of the second mounting steps 32 are gradually lowered along the center of the hemispherical outer wall of the base 11, and a height difference is provided between the two adjacent second mounting steps 32. Specifically, the first mounting step 31 and the second mounting steps 32 cooperated with the screws 14 and the pre-tighten screws 15 to mount at intervals all of the first circuit board 22 and the second circuit boards 23, which improves the interval effect between adjacent circuit boards and prevent the mutual interference between the first, circuit board 22 and the second circuit boards 23, or between the adjacent second circuit boards 23.

Referring to FIG. 8, in another embodiment, the through holes 24 are designed as long holes, evenly distributed on the base 11. A portion of the through holes 24, respectively aligned with the corresponding second circuit, boards 23, are arranged in an arc-shaped structure. The other portion of the through holes 24, aligned with the first circuit board 22, are arranged in a linear structure. Specifically, the number of the light sources 21 contained in the through holes 24 can be changed according to the requirement to the light intense. Each of the through holes 24 can be mounted as least one of the light sources 21. These structure effectively improves the distributed operability of the light sources 21. Compared with the hair-growing instrument using the fixed hole structure, the through holes 24 with the long hole structure can accommodate multiple groups of the light sources 21, effectively improving the light intensity.

Figure 11:
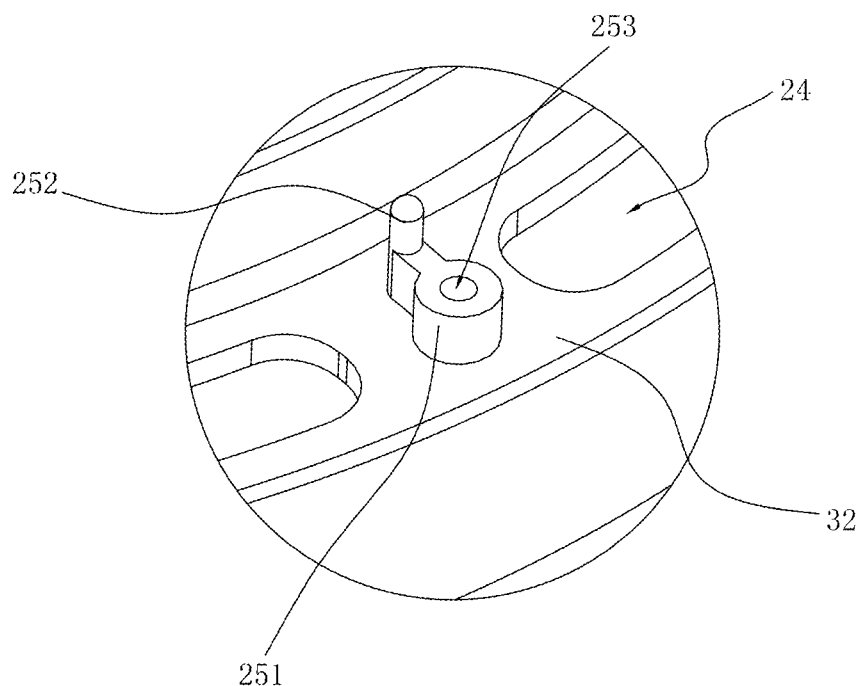
FIG. 11 is an enlarge view of A part in FIG. 8.

Referring to FIG. 11, in the other embodiment, each of the studs 25 includes a column body 251 and a positioning pin 252. The column body 251 is, provided with a threaded hole 253, The column body 251 is fixed on the second circuit boards 23. The positioning pin 252 is fixed on a side of the column body 251. The height of the positioning pin 252 is greater than the studs 25, each of the second circuit boards 23 is provided with a positioning hole clamped with the positioning pin 252. Before the second circuit boards 23 locks on the column body 251, it is fixed by the positioning pin 252 to effectively prevent the second circuit board 23 from mounting a bias.

Referring to FIG. 1, in another embodiment, the base 11 is provided with a human body sensing mechanism 60 towards the user's head, contained in the cavity 13. The output end of the human body sensing mechanism 60 is electrically connected with the circuit control 51. Specifically, if the user accidentally takes dove the hair growing instrument, the human body sensing mechanism 60 can obtain the information and then feedback the information to the circuit control 51, which disconnects the power supply to turn off the hair growing instrument. Compared with the hair growing instrument that continues to shine after leave the user's head and the electricity is easy to run out, the hair growing instrument adopts the human body sensing mechanism 60 can avoid the occasions, which improves the practically.

Figure 7:
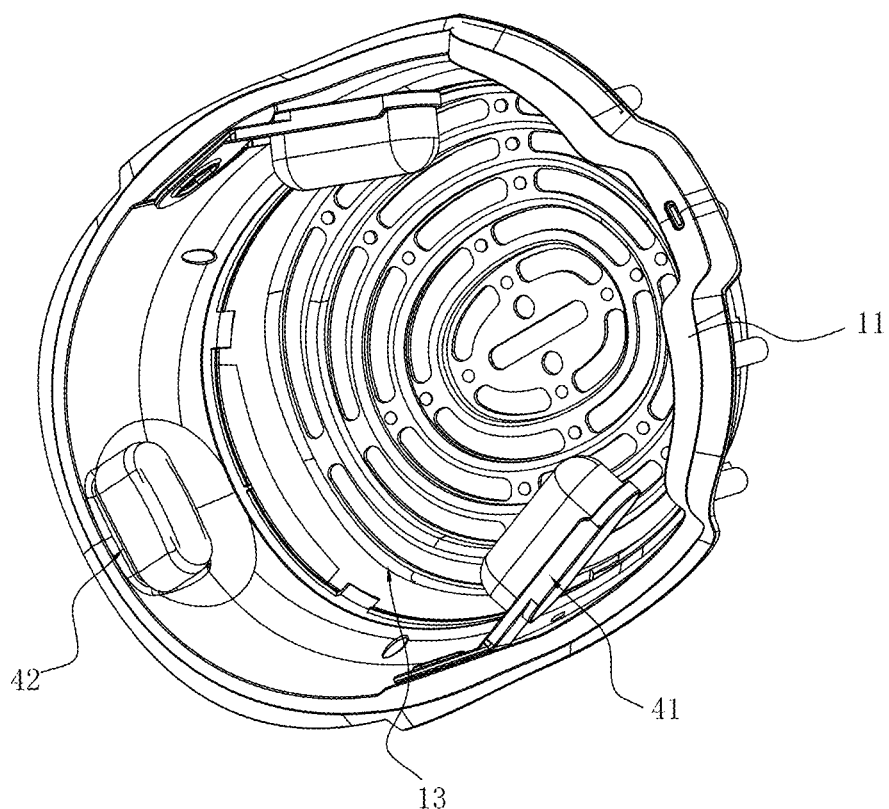
FIG. 7 is a perspective view of the clamp mechanism 40 according to the invention.
Figure 13:
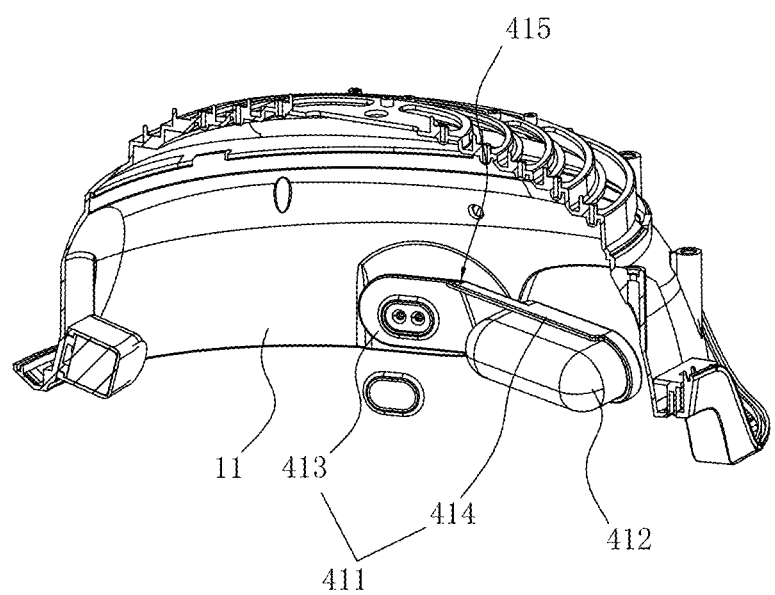
FIG. 13 is a perspective view of the sensing unit taking off the base according to the invention.

Referring to FIG. 1, FIG. 7 and FIG. 13, in another embodiment, the inner wall of the base 11 is provided with a clamp mechanism 40 which includes two lateral forehead assemblies 41 and a frontal forehead assembly 42. The two lateral forehead assemblies 41 are symmetrically positioned along the opening, edge of the cavity 13 and align with the left and right forehead of the user, respectively. The frontal forehead assembly 42 is disposed at the opening edge of the cavity 13 and align to the frontal forehead of the user. A holding slot capable of holding the user's head is formed between the lateral forehead assemblies 41 and the frontal forehead assembly 42. The human body sensing mechanism 60 is provided on the lateral forehead assemblies 41.

Specifically, when the user's head enters the cavity 13, firstly the frontal forehead assembly 42 is against the frontal forehead of the user, then the lateral forehead assemblies 41 are against the lateral foreheads of the user. The hair growing instrument is fixed on the user's head through the three-point positioning way, which improve the stability of the hair growing instrument.

Figure 3:
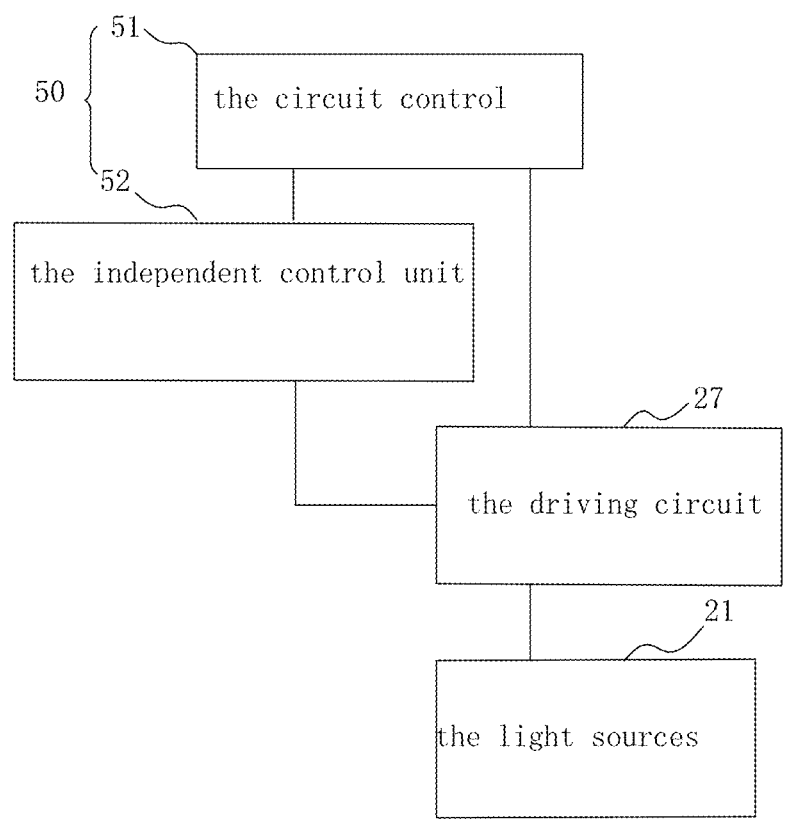
FIG. 3 is a circuit construction block of the stable smart laser hair-growing instrument with independent light sources according to the invention.

Referring to FIG. 3, in another embodiment, the lateral forehead assemblies 41 includes a mounting frame 411 and a cushion 412. The mounting frame 411 is disassembly mounted on the inner wall of the base 11. Then end of the mounting frame 411 is provided with a bending part 415, the bending part 415 extends towards the cavity 13, the cushion 412 is fixed on the bending part 415. Wherein, the bending part 415 and the mounting frame 411 are made of elastic material, and the cushion 412 is made of sponge or silicone.

Specifically, the mounting frame 411 includes a connecting plate 413 and an elastic plate 414. The connecting plate 413 and the elastic plate 414 are cast by a metal material through a die casting machine. The connecting plate 413 is fixed on the inner wall of the base 11 by the screw 14. The elastic plate 414 is disposed on the connecting plate 413. The bending plate 415 is located between the connecting plate 413 and the elastic plate 414. The elastic plate 414 is made from elastic and metal material. The elastic plate 414 extends in the cavity 13. The cushion 412 is fixed on a side surface, facing a centre of the cavity 13, of the elastic plate 414. The cushion 412 is made of a soft material such as sponge, leather or silicone. The side surface of the cushion 412 away from the elastic plate 414 is arranged in a curved configuration to fit the head shape of the user.

Figure 14:
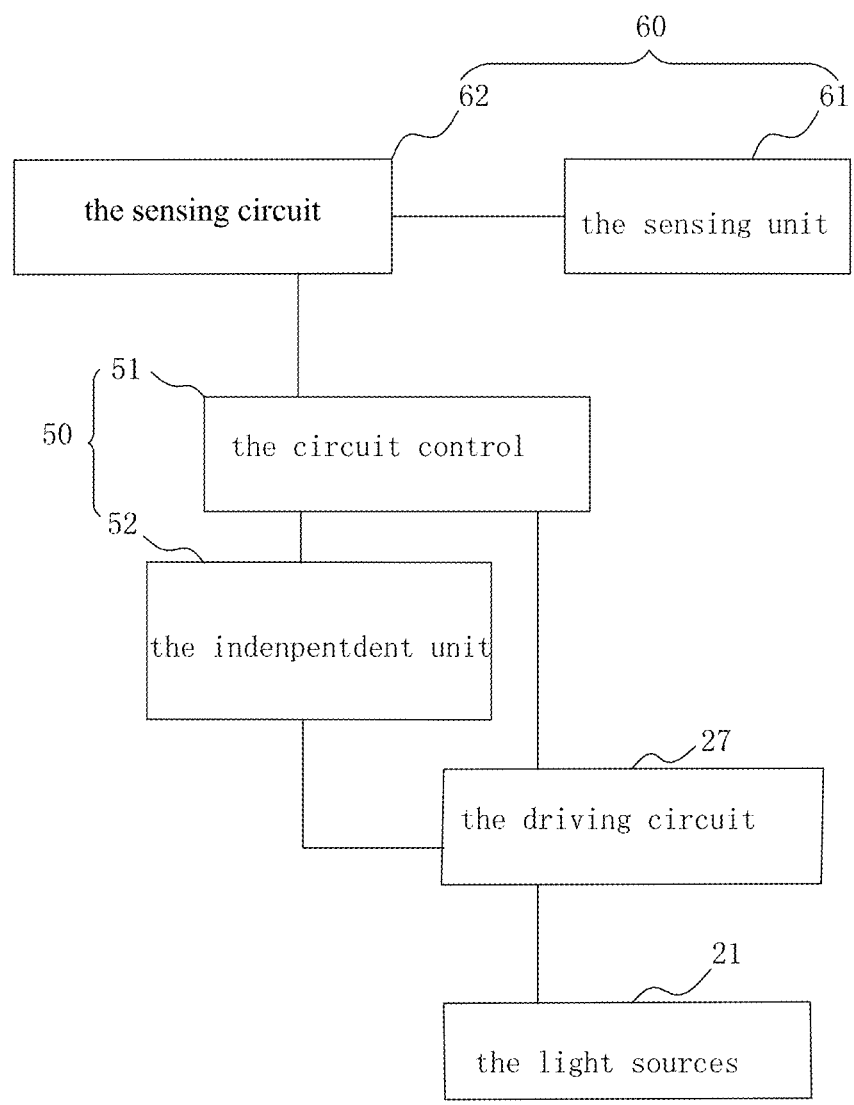
FIG. 14 is a circuit construction block of the stable smart laser hair-growing instrument, with independent light sources with a human sensing mechanism according to the invention.

In another embodiment, referring to FIG. 14, the human sensing mechanism 60 includes a sensing circuit 62 and a sensing unit 61. The sensing circuit 62 is disposed in the shell 10. The sensing unit 61 is fixed on the lateral forehead assembly 41. The sensing circuit is electrically connected with the circuit control 51. The sensing unit 61 is either a pressure sensor or an infrared sensor.

In an embodiment, the sensing unit 61 is a pressure sensor. The pressure sensor is disposed between the connecting plate 413 and the inner wall of the base 11. The sensing end of the pressure sensor is connected against the connection plate 413. When the user wears the hair growing instrument, the head of the user overcomes the elasticity of the elastic plate 414 and pushes the connecting plate 413 toward the inner wall of the base 11. The connecting plate 413 works on the sensing end of the pressure sensor, which feeds the pressure coefficient to circuit master 51. When the user takes off the hair growing instrument, the pressure on the pressure sensor disappear. The pressure sensor feeds back the corresponding pressure conversion signal to the circuit control 51, which drives the hair growing instrument to stop operation.

Figure 12:
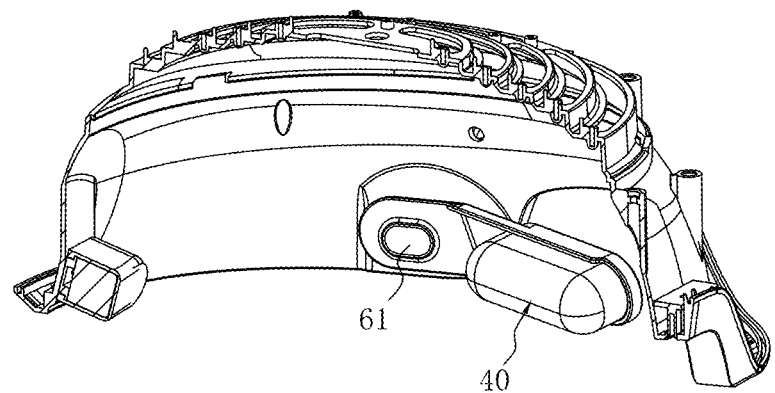
FIG. 12 is a perspective view of the clamp mechanism and the base according to the invention.

In the other embodiment, referring to FIG. 12, the sensing unit 61 is an infrared sensor. The connecting plate 413 is mounted on the inner wall of the base 11 by screws 14. The sensing unit 61 is disposed on the connecting plate 413. The sensing end of the sensing unit 61 faces to the cavity 13. When the head of the user appears at the sensing end of the sensor unit 61, the circuit master 51 drives the hair growing instrument to operate.

The above is only a better embodiment of the invention and is not used to limit the invention, and any modification, equivalent replacement and improvement made within the spirit and principles of the invention shall be included in the scope of protection of the invention.

What is claimed:

1. A stable smart laser hair-growing instrument with independent light sources, wherein comprising:
    a shell, having a cavity disposed above a user's head;
    a laser emitting assembly, comprising light sources, a first circuit board and multiple second circuit boards; said first circuit board is disposed in said shell at a position aligned at a center of a user head; said multiple second circuit boards are multiple rings with concentric axes, arranged up and down, in adjacent two rings, an outer diameter of one at below is bigger than that of the other at above; a gap is arranged between said adjacent two rings; said light sources are evenly distributed on an end surface, facing said user's head, of said first circuit board and those of said second circuit boards; said first circuit board and each of said second circuit boards are provided with a driving circuit, respectively; said light sources are electrically connected with said corresponding driving circuit;
    a control system, comprising a circuit control and a multi-group of independent control units electrically connected with said circuit control; all said independent control units are electrically connected to said corresponding driving circuit of said second circuit boards and that of said first circuit board, respectively;
    wherein said shell includes a base and a frame; said cavity is formed in said base, said frame is disassembly connected with an end of said base away from said cavity; said first circuit board and said second circuit boards are arranged between said base and said frame; said base is provided with multiple of through holes, each aligned to one of said corresponding light sources, said lights of said light sources can pass through said through holes and enter said cavity.

2. The stable smart laser hair-growing instrument with independent light sources according to claim 1, wherein each of said light sources includes a light-emitting LED and a laser light unit, which are integrated on said second circuit boards or said first circuit board, and electrically connected with said driving circuit on said correspondingly circuit boards.

3. The stable smart laser hair-growing instrument with independent light sources according to claim 2, wherein each of said light sources also includes a loading unit for assembling said light-emitting LED and said laser light unit; said loading unit is fixed on said second circuit boards or on said first circuit board; said loading unit is a seal sleeve structure filled with xenon.

4. The stable smart laser hair-growing instrument with independent light sources according to claim 3, wherein a multiple of said loading units are welded on said second circuit boards; said multiple of said loading units assembled with said light-emitting LED and said laser light units are arranged at intervals along said rings of said second circuit boards, each of said second circuit boards and said corresponding light sources on it form an annular lamp strip structure.

5. The stable smart laser hair-growing instrument with independent light sources according to claim 1, wherein said through holes are designed as long holes, evenly distributed on said base; a portion of said through holes, respectively aligned with said corresponding second circuit boards, are arranged in an arc-shaped structure; said other portion of said through holes, aligned with said first circuit board, are arranged in a linear structure.

6. The stable smart laser hair-growing instrument with independent light sources according to claim 1, wherein said base is provided with a human body sensing mechanism towards said user's head, contained in said cavity; an output end of said human body sensing mechanism is electrically connected with said circuit control;
    said human sensing mechanism includes a sensing circuit and a sensing unit; said sensing circuit is disposed in said shell; said sensing unit is fixed on two lateral forehead assemblies; said sensing circuit is electrically connected with said circuit control; said sensing unit is either a pressure sensor or an infrared sensor.

7. The stable smart laser hair-growing instrument with independent light sources according to claim 6, wherein an inner wall of said base is provided with a clamp mechanism which includes two lateral forehead assemblies and a frontal forehead assembly; said two lateral forehead assemblies are symmetrically positioned along an opening edge of said cavity and aligned with said left and right forehead of said user, respectively; said frontal forehead assembly is disposed at said opening edge of said cavity and aligned to said frontal forehead of said user; a holding slot capable of holding said user's head is formed between said lateral forehead assemblies and said frontal forehead assembly; said human body sensing mechanism is provided on said lateral forehead assemblies.

8. The stable smart laser hair-growing instrument with independent light sources according to claim 7, wherein each of said lateral forehead assemblies includes a mounting frame and a cushion; said mounting frame is disassembly mounted on said inner wall of said base; an end of said mounting frame is provided with a bending part, said bending part extends towards said cavity, said cushion is fixed on said bending part; said bending part and said mounting frame are made of elastic material, and said cushion is made of sponge or silicone.

* * * * *